(12) United States Patent
Chen et al.

(10) Patent No.: US 7,423,166 B2
(45) Date of Patent: Sep. 9, 2008

(54) STABILIZED CYCLOSILOXANES FOR USE AS CVD PRECURSORS FOR LOW-DIELECTRIC CONSTANT THIN FILMS

(75) Inventors: Tianniu Chen, Rocky Hill, CT (US); Chongying Xu, New Milford, CT (US); Thomas H. Baum, New Fairfield, CT (US); Ravi K. Laxman, San Jose, CA (US); Alexander S. Borovik, W. Hartford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 466 days.

(21) Appl. No.: 10/650,282

(22) Filed: Aug. 28, 2003

(65) Prior Publication Data

US 2004/0039219 A1 Feb. 26, 2004

Related U.S. Application Data

(63) Continuation-in-part of application No. 10/015,326, filed on Dec. 13, 2001, now Pat. No. 7,108,771, and a continuation-in-part of application No. 10/301,109, filed on Nov. 21, 2002.

(51) Int. Cl.
*C07F 7/08* (2006.01)
(52) U.S. Cl. ..................................... 556/464
(58) Field of Classification Search .................. 556/460
See application file for complete search history.

(56) References Cited

U.S. PATENT DOCUMENTS

| | | | |
|---|---|---|---|
| 4,087,448 A | 5/1978 | Rossmy et al. | |
| 4,127,598 A | 11/1978 | McEntee | |
| 4,156,689 A | 5/1979 | Ashby et al. | |
| 4,374,110 A | 2/1983 | Darnell et al. | |
| 4,670,299 A | 6/1987 | Fukuyama et al. | |
| 4,745,169 A | 5/1988 | Sugiyama et al. | |
| 4,755,370 A | 7/1988 | Kray et al. | |
| 4,764,631 A | 8/1988 | Halm et al. | |
| 4,871,616 A | 10/1989 | Kimura et al. | |
| 5,043,789 A | 8/1991 | Linde et al. | |
| 5,047,492 A | 9/1991 | Weidner et al. | |
| 5,098,865 A | 3/1992 | Machado et al. | |
| 5,204,314 A | 4/1993 | Kirlin et al. | |
| 5,210,250 A | 5/1993 | Watanuki et al. | |
| 5,276,173 A | 1/1994 | Marko et al. | |
| 5,281,686 A * | 1/1994 | Blohm et al. .................. 528/25 |
| 5,312,947 A | 5/1994 | Tsukuno et al. | |
| 5,484,867 A | 1/1996 | Lichtenhan et al. | |
| 5,536,323 A | 7/1996 | Kirlin et al. | |
| 5,711,816 A | 1/1998 | Kirlin et al. | |
| 5,804,040 A | 9/1998 | Asai et al. | |
| 6,114,500 A | 9/2000 | Mori et al. | |
| 6,147,009 A | 11/2000 | Grill et al. | |
| 6,171,945 B1 | 1/2001 | Mandal et al. | |
| 6,331,494 B1 | 12/2001 | Olson et al. | |
| 6,368,359 B1 | 4/2002 | Perry et al. | |
| 6,383,955 B1 | 5/2002 | Matsuki et al. | |
| 6,410,463 B1 | 6/2002 | Matsuki | |
| 6,451,712 B1 | 9/2002 | Dalton et al. | |
| 6,486,082 B1 | 11/2002 | Cho et al. | |
| 6,495,479 B1 | 12/2002 | Wu et al. | |
| 6,858,697 B2 | 2/2005 | Mayorga et al. | |
| 6,936,551 B2 | 8/2005 | Moghadam et al. | |
| 7,011,864 B2 | 3/2006 | Ishida | |
| 2003/0044531 A1 | 3/2003 | Ishida | |
| 2003/0077918 A1 | 4/2003 | Wu et al. | |
| 2003/0124785 A1 | 7/2003 | Xu et al. | |
| 2003/0146451 A1 | 8/2003 | Huang et al. | |
| 2003/0232137 A1 | 12/2003 | Vrtis et al. | |
| 2004/0054114 A1 | 3/2004 | Mayorga et al. | |
| 2004/0071878 A1 | 4/2004 | Schuhmacher et al. | |
| 2004/0087184 A1 | 5/2004 | Mandal et al. | |
| 2004/0101633 A1 | 5/2004 | Zheng et al. | |
| 2004/0156987 A1 | 8/2004 | Yim et al. | |
| 2005/0130404 A1 | 6/2005 | Moghadam et al. | |
| 2005/0181613 A1 | 8/2005 | Xu et al. | |
| 2005/0268849 A1 | 12/2005 | Ishida | |

FOREIGN PATENT DOCUMENTS

| | | |
|---|---|---|
| EP | 0543665 | 5/1993 |
| EP | 1 321 469 A1 | 6/2003 |

(Continued)

OTHER PUBLICATIONS

Mantz, et al., "Thermolysis of Polyhedral Oligomeric Silsesquioxane (POSS) Macromers and POSS-Siloxane Copolymers", Chem. Mater., 1996, 8, p. 1250-1259.

(Continued)

*Primary Examiner*—Samuel Barts
(74) *Attorney, Agent, or Firm*—Steven J. Hultquist; Intellectual Property/Technology Law; Maggie Chappuis

(57) ABSTRACT

A siloxane dielectric precursor for use in a chemical vapor deposition (CVD) process, which has been dosed with a stabilizing agent(s) selected from free-radical inhibitors, end-capping agents and mixtures thereof. The stabilized siloxane dielectric precursor reduces the occurrence of premature deposition reactions occurring in the heated environment of the CVD delivery lines and process hardware.

36 Claims, 6 Drawing Sheets

FOREIGN PATENT DOCUMENTS

| | | | |
|---|---|---|---|
| EP | 1321469 | A | 6/2003 |
| JP | 50-111198 | | 1/1974 |
| WO | 98/15499 | A | 4/1998 |
| WO | 2004/027110 | A | 4/2004 |
| WO | WO 2004/027110 | A2 | 4/2004 |

OTHER PUBLICATIONS

Ravi K. Laxman, Neil Hendrix Barry Arkles, Terry A. Tabler "Synthesizing Low-K CVD Materials for Fab Use" Semiconductor International, Nov. 1, 2000.

Alfred Grill, et al., Novel Low-k Dual-Phase Materials Prepared by PECVD, Mat. Res. Soc. Symp. Proc. vol. 612, 2000 Materials Research Society.

Albert Wang, et al. "TMCTS for Gate Dielectric in Thin Film Transistors", Mat. Res. Soc. Meeting 1996.

A. Grill, et al., "Ultralow-k Dielectrics Prepared by Plasma-enhanced Chemical Vapor Deposition", Applied Physics Letters, vol. 79, No. 6, Aug. 6, 2001.

U.S. Appl. No. 10/015,326, filed Dec. 31, 2001, Chongying Xu, et al.

U.S. Appl. No. 10/301,109, filed Nov. 21, 2002, Alexander S. Borovik.

* cited by examiner

STABILIZED CYCLOSILOXANES FOR USE AS CVD PRECURSORS FOR LOW-DIELECTRIC CONSTANT THIN FILMS

RELATED APPLICATION INFORMATION

This application is a continuation in part of Applicant's U.S. patent applications, Ser. No. 10/015,326, filed Dec. 13, 2001, now U.S. Pat. No. 7,108,771 entitled, "Method for Removal of Impurities in Cyclic Siloxanes Useful as Precursors for Low Dielectric Constant Thin Films" and Ser. No. 10/301,109, filed on Nov. 21, 2002, entitled "Porogen Material"

TECHNICAL FIELD OF THE INVENTION

The present invention relates generally to a method for stabilizing siloxanes, particularly, cyclosiloxanes, such as tetramethylcyclotetrasiloxane (TMCTS) useful as CVD precursors to low-dielectric constant (k) thin films, as well as to a method for deposition of low dielectric constant thin films from the stabilized siloxane or cyclosiloxane precursor.

BACKGROUND OF THE INVENTION

As the need for integrated circuits for semiconductor devices having higher performance and greater functionality increases, device feature geometries continue to decrease. As device geometries become smaller, the dielectric constant of an insulating material used between conducting paths becomes an increasingly important factor in device performance.

As device dimensions shrink to less than 0.25 µm, propagation delay, cross-talk noise and power dissipation due to resistance-capacitance (RC) coupling become significant due to increased wiring capacitance, especially interline capacitance between parallel metal lines on the same level. These factors all depend critically on the dielectric constant of the separating insulator or inter-layer dielectric (ILD).

The use of low dielectric constant (k) materials advantageously lowers power consumption, reduces cross-talk, and shortens signal delay for closely spaced conductors through the reduction of both nodal and interconnect line capacitances. Dielectric materials that exhibit low dielectric constants (k) are critical in the development path toward faster and more power efficient microelectronics.

In order to enhance performance of circuit features such as the noted parallel metal lines, a decrease in capacitance may be sought. In order to decrease capacitance the particular ILD employed to isolate the metal lines is often of a 'low-k' character. That is, where capacitance (C) is k∈A/d, with a permittivity constant (∈), a distance (d) between the parallel metal lines, and an interfacing area (A) of the metal lines with respect to one another, capacitance (C) may be lowered where the dielectric constant (k) is reduced. As semiconductor features continue to become smaller and smaller, with the distance (d) continuing to be reduced, the use of 'low-k' materials in order to reduce capacitance (C) is becoming increasingly important. Generally, a low-k ILD may be an ILD with a dielectric constant (k) that is below about 4.

Siloxanes, particularly cyclosiloxanes, such as 2,4,6,8-tetramethylcyclotetrasiloxane (TMCTS), are being evaluated aggressively for obtaining low-k thin-films as interlayer dielectrics in an integrated circuit by a plasma enhanced chemical vapor deposition (PECVD) approach.

Materials deposited from the cyclosiloxanes result in SiCOH-containing films with Si—CH$_3$ retained in a cross-linking polymeric type networking structure. Generally, Si—CH$_3$ moiety in low-k films is believed to advantageously lower the dielectric constant to values ranging from about 2.4 to 3.2.

The purification and reproducible delivery of these precursor materials for use in PECVD processes is extremely critical for full-scale commercial production. And present deposition processes, specifically with respect to TMCTS suffer from irreproducible delivery due to pre-mature polymerization of the TMCTS precursor within the delivery lines and process hardware.

The premature polymerization reactions occur in heated process environments and/or in the presence of impurities such as water/moisture, Lewis acids and Lewis bases, which with respect to impurities may be introduced into the process environment through various routes such as, raw material synthesis. Manufacture of cyclosiloxanes often results in residual reactants and by-products remaining in the product-stock material, as trace impurities, (e.g. water and partially halogenated or chlorinated silicon species) which if not removed will serve to catalyze the aforementioned polymerization mechanisms in the process delivery lines and hardware.

The PECVD film deposition process environment serves as a further source for the introduction of impurities, where for example, O$_2$ and CO$_2$ containing radicals, generated by the plasma, back-stream into the delivery lines and react with cyclosiloxane molecules to initiate ring-opening and polymerization reactions.

Moreover, catalytic impurities may be introduced to the PECVD process as residual gas species from, for example, a prior cleaning or deposition step. In certain aspects of circuit manufacture, differing steps may be performed on a wafer, in series and in a single PECVD chamber, such as, deposition of a low-k film followed by deposition of a SiN, etch-stop layer. In a typical etch-stop layer deposition step, SiN precursors such as, silanes, chlorosilanes, alkylsilanes, and ammonia (NH$_3$) may be used. And although the CVD tool is purged between steps, residual process gas, particularly ammonia, remains in the process lines, in concentrations sufficient to catalyze the ring-opening and/or polymerization mechanisms of the cyclosiloxane materials in the process hardware and delivery lines.

Accordingly, there is a need in the art to improve the purity of these cyclosiloxane materials by reducing the concentration of water and other catalytic species from therein and to improve their stability and utility during processing in order to minimize the degree to which polymerization occurs in the delivery lines and process hardware.

It would therefore be a significant advance in the art to provide such cyclosiloxane materials and corresponding processes, which are not prone to catalytic polymerization reactions as described hereinabove.

SUMMARY OF THE INVENTION

The present invention relates to the purification and stabilization of siloxanes, particularly cyclosiloxanes, in connection with the use of such materials as chemical reagents.

In one aspect, the invention relates to a stabilized siloxane material for use as a dielectric precursor.

In a further aspect the invention relates to a process for stabilizing a siloxane material by dosing the siloxane material with at least one of, a free radical inhibitor and an end-capping reagent.

In a still further aspect, the present invention relates to a process comprising delivering a stabilized siloxane-based dielectric precursor to a semiconductor substrate to form a dielectric material thereon.

Other aspects, features and embodiments of the invention will be more fully apparent from the ensuing disclosure and appended claims.

DETAILED DESCRIPTION

While embodiments are described with reference to certain circuit features isolated by a dielectric film, embodiments may be applicable to any circuit feature to be isolated by the film formed in part by utilizing a stabilized siloxane reagent. Additionally, embodiments may be particularly useful when multiple circuit features are to be isolated by the same dielectric film.

Although described hereinafter primarily in reference to specific cyclosiloxanes, it will be appreciated that the method of the invention is not thus limited, but rather is broadly applicable to the stabilization of other siloxane materials, as well as mixtures of the foregoing. The ensuing discussion relating to cyclosiloxanes should therefore be understood to encompass such other siloxane materials, as variant feedstocks to which the stabilization methodology of the invention is usefully applied.

The present invention provides a stabilized cyclosiloxane dielectric precursor, suitable for semiconductor device manufacturing applications, wherein the cyclosiloxane dielectric precursor is used for producing porous, low-dielectric constant, SiCOH thin films of correspondingly high purity.

Figure 1:
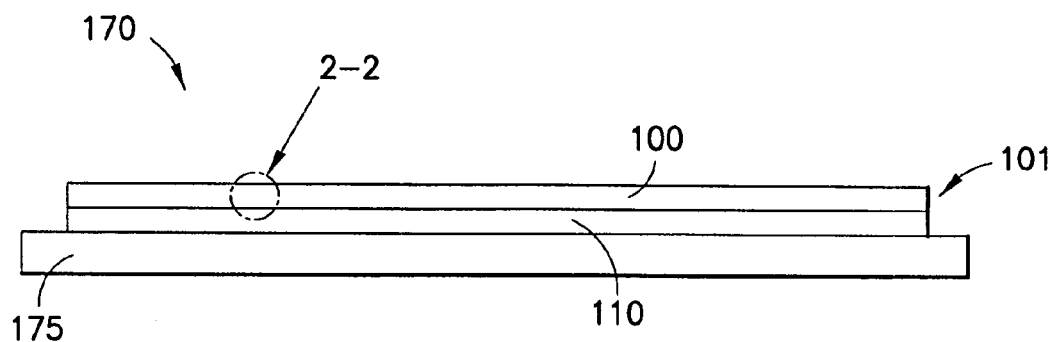
FIG. 1 is a side view of a semiconductor wafer having a porous film formed thereon.

Referring to FIG. 1, an embodiment of a semiconductor wafer 101 is shown. The semiconductor wafer 101 includes a substrate 110 which may be silicon or other conventional semiconductor material. An embodiment of a dielectric film 100 is shown on the substrate 110. The film 100 is of substantial uniformity and/or porosity, which advantageously result in a substantially uniform dielectric constant value being present throughout the film 100. As described further herein, the presence of such a uniform dielectric constant value throughout the film 100 helps to enhance the reliability of circuit features to be isolated by the material of the dielectric film 100.

The dielectric film 100 shown in FIG. 1 is formed by vapor depositing a stabilized cyclosiloxane material above the semiconductor wafer 101 as described further herein. For example, heat may be applied through a susceptor 175 of a conventional semiconductor oven 170 in order to induce a chemical and physical change in the deposited dielectric material, such that it is transformed into a porous film 100 as shown.

Embodiments of the dielectric material described above may be delivered to the semiconductor wafer 101 by conventional means. For example, in one embodiment the semiconductor wafer 101 may be placed in a conventional chemical vapor deposition (CVD) apparatus where a gas mixture, including components of the stabilized cyclosiloxane material and other filler gasses are introduced. A source of radio frequency (RF) energy may even be applied to provide plasma enhanced CVD (i.e. PECVD). Conventional pressures, RF, and temperatures, described further below, may be applied during delivery of the stabilized cyclosiloxane material.

Figure 2:
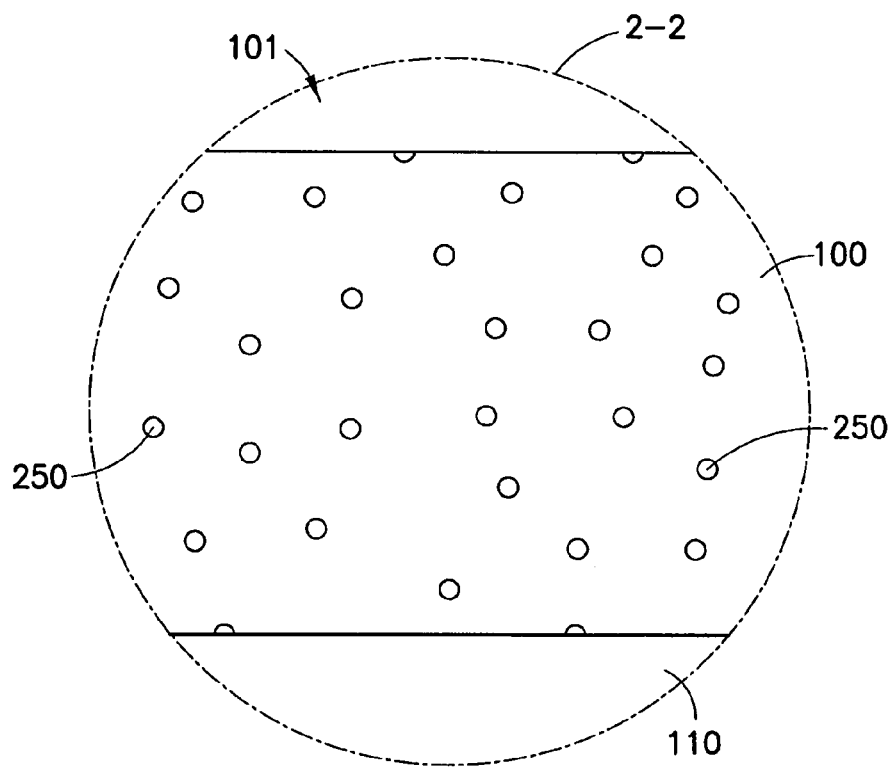
FIG. 2 is an exploded view of a portion of the semiconductor wafer taken from 2-2 of FIG. 1.

Continuing with reference to FIGS. 1 and 2, the dielectric film 100 is shown having substantially uniform porosity as noted above. That is, pores 250 are distributed fairly uniformly throughout the film 100. As described further herein, this will lead to a more uniform and predictable dielectric constant, and thus, more reliable device performance.

In order to ensure that the dielectric film, 100 is deposited in a substantially uniform layer, the dielectric material itself must be deposited from a stable silicon based precursor composition, which when delivered to the semiconductor wafer 101 as described above is absent any premature polymerization reactions.

Preferably, the stabilized silicon based dielectric precursor comprises a cyclosiloxane composition such as tetramethylcyclotetrasiloxane (TMCTS), hexamethylcyclotetrasiloxane (HMCTS), octamethylcyclotetrasiloxane (OMCTS), and others dosed with a stabilizing agent, which may include a free-radical inhibitor and/or a stabilizing reagent. The stabilized cyclosiloxane dielectric precursor may be delivered to the vicinity of the semiconductor wafer 101 through conventional CVD or other deposition methods. In this manner, the cyclosiloxane dielectric precursor, having been stabilized by at least one free-radical inhibitor and/or stabilizing reagent, is delivered to and deposited on the wafer surface minus detrimental premature polymerization in the process delivery lines and/or at the wafer surface.

Continuing again with reference to FIGS. 1 and 2, the semiconductor wafer 101 is shown on a susceptor 175 of a conventional semiconductor bake oven 170. In one embodiment, the susceptor 175 heats the semiconductor wafer 101 changing the deposited dielectric material into a porous dielectric SiCOH film 100 with substantially uniformly distributed pores 250 as shown in FIG. 2. The heat provided by the susceptor 175 may be between about 100° C. and about 450° C., preferably below about 400° C. However, the exact temperature applied as well as the amount of time heat is applied are a matter of design choice. For example, where increased porosity and a lower dielectric constant value are paramount, the time and extent of heat application will similarly be higher.

The overall level of porosity to be activated may be particularly tailored by the exact composition of the cyclosiloxane material itself in addition to process parameters such as temperature. Regardless of the degree of porosity formed, the pores 250 will remain substantially uniformly distributed throughout the porous film 100.

With reference to FIGS. 3A-3D, the formation of metal lines 392 isolated by a dielectric film 300, which is preferably porous, is discussed in detail. The embodiments described with reference to such figures describe the formation of particular circuit features (metal lines 392) isolated by the dielectric film. However, additional circuit features may be formed and isolated by the dielectric film 300. Additionally, FIG. 4 is a flow chart summarizing embodiments of forming the metal line 392 in a semiconductor wafer 301 as described in FIGS. 3A-3D and is referenced throughout remaining portions of the description as an aid in describing such embodiments.

Figure 3A:
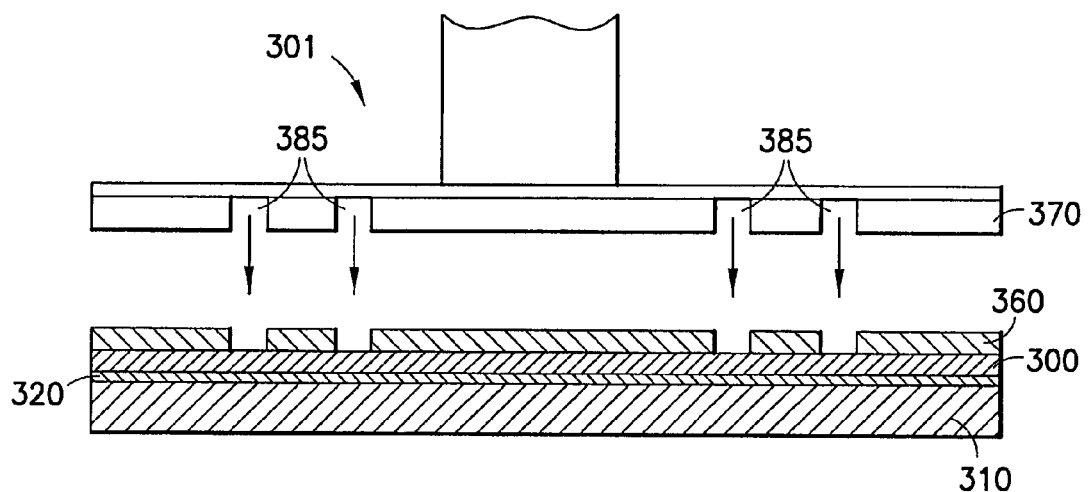
FIG. 3A is a side cross-sectional view of a semiconductor wafer having a patterned photoresist formed above a porous film.
Figure 4:
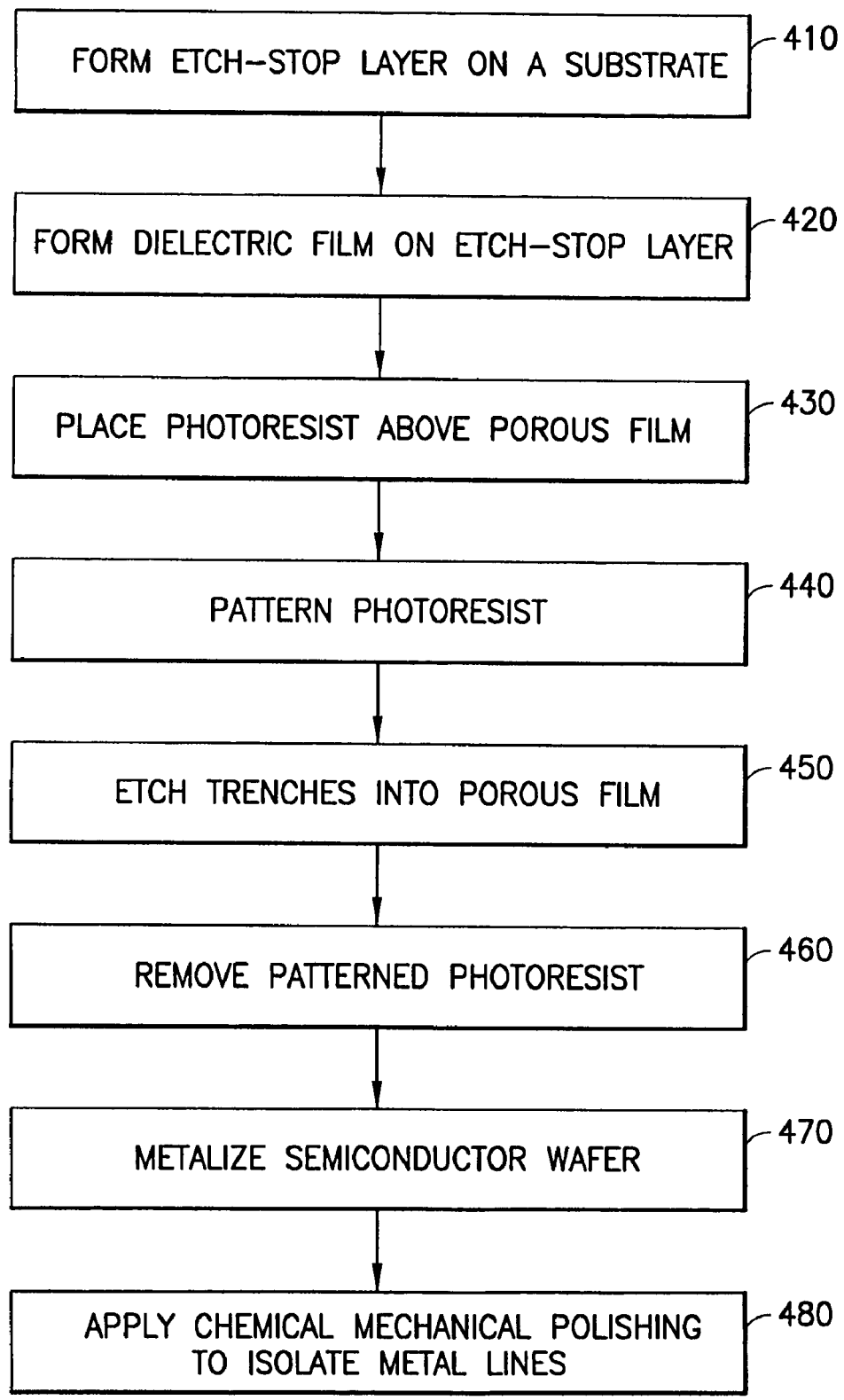
FIG. 4 is a flow chart summarizing embodiments of isolating patterned semiconductor circuitry with a porous silicon based dielectric composition.

Referring now to FIG. 3A, a semiconductor wafer is shown having a thin conformal layer of SiN 320, which will serve as an etch-stop layer to a subsequent dielectric deposition step as indicated at 410 of FIG. 4. The deposition of the etch-stop layer may be achieved by conventional techniques such as CVD where, for example, a mixture of trimethylsilane, $(CH_3)_3SiH$ and ammonia $(NH_3)$ are co-vapor deposited onto the substrate 310, until which time the conforming layer 320 is formed.

In a subsequent deposition step a dielectric film 300 is formed onto the etch-stop layer 320 as indicated at 420 of FIG. 4. The dielectric film 300 is deposited from a stabilized cyclosiloxane dielectric precursor, which may be formed onto the stop-etch layer according to methods described above with reference to FIGS. 1 and 2 and includes a substantially uniform dielectric constant value throughout.

A chemically resilient photoresist 360 is placed above the dielectric film 300 as indicated at 430. The photoresist 360 is then patterned as indicted at 440 with a photo-masking tool 301 as shown in FIG. 3A. In the embodiment shown, the photoresist 360 is subject to deterioration upon exposure to certain conditions such as ultraviolet (UV) light. Therefore, in order to pattern the photoresist 360, the photo-masking tool 301 includes UV emitting portions 385 defined and contained by a mask 370. In this manner the photo-masking tool 301 may be applied to pattern the photoresist 360 as shown in FIG. 3A.

Figure 3B:
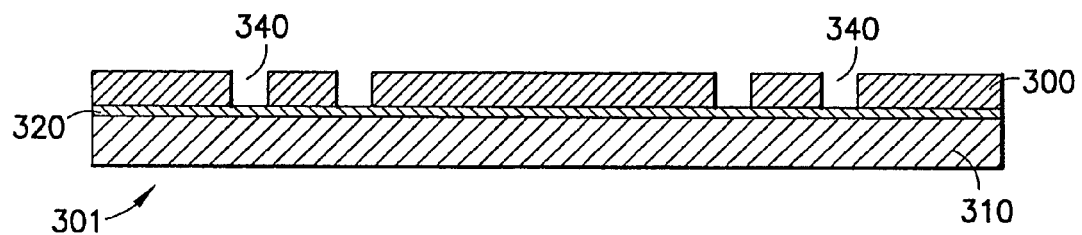
FIG. 3B is a side cross-sectional view of the semiconductor wafer of FIG. 3A having trenches formed in the porous film.

Conventional etching techniques may follow the patterning of the photoresist 360. That is, as indicated at 450 of FIG. 4, conventional chemical-etchants may be delivered to the semiconductor wafer 301 to form trenches 340 in the dielectric film 300. The patterned photoresist 360 protects the dielectric film 300 where present. However, the patterning described above, allows chemical etchants to reach the dielectric film 300 at certain locations where the trenches 340 are formed. Once the trenches 340 are formed, the patterned photoresist 360 may be removed as indicated at 460 of FIG. 4. This may be achieved for example by further exposure to UV light, leaving the semiconductor wafer 301 as shown in FIG. 3B.

Figure 3C:
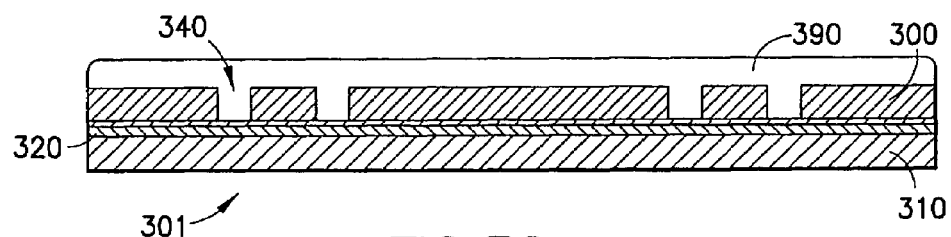
FIG. 3C is a side cross-sectional view of the semiconductor wafer of FIG. 3B following metallization.

Referring to FIGS. 3C and 4, the semiconductor wafer 301 is metallized as indicated at 470. For example, copper, aluminum, or other electrically conductive material may be deposited above the substrate 310, dielectric film 300 and barrier/adhesion layer 320, while filling trenches 340. This may be achieved by conventional techniques such as CVD as described above and/or electroplating. The resulting metal layer 390 remains to be isolated and formed into independent circuit features as described below.

Figure 3D:
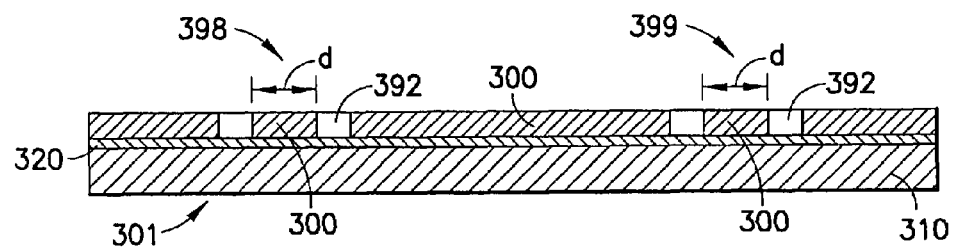
FIG. 3D is a side cross-sectional view of the semiconductor wafer of FIG. 3C following application of chemical mechanical polishing to isolate pairs of metal lines.

Referring to FIG. 3D the semiconductor wafer 301 is shown following the application of conventional chemical mechanical polishing (CMP) to isolate circuit features in the form of metal lines 392 as indicated at 480 of FIG. 4. That is, a chemical slurry is delivered, and a rotating polishing pad applied, to the semiconductor wafer 301 until the metal lines 392 are left isolated by the dielectric film 300.

Continuing with reference to FIG. 3D, a first pair 398 of metal lines 392 at one location of the semiconductor wafer 301 may be compared to a second pair 399 at another location. Each pair 398, 399 includes metal lines 392 separated by dielectric film 300 of a distance (d). While the pairs 398, 399 are located in entirely different areas of the semiconductor wafer 301, the dielectric film 300, formed according to methods described herein, is substantially uniform throughout.

From one portion of the film 300 to another, the dielectric constant (k) value remains substantially consistent. That is, the dielectric constant (k) value for the first pair 398 of metal lines 392 is substantially equivalent to the dielectric constant value (k) for the second pair 399. As a result, capacitance (C) (which is k∈A/d) is less variable. Resulting circuit features, such as the metal lines 392, isolated by the dielectric film 300, therefore perform in a more reliable and predictable manner. Further processing may follow wherein the semiconductor wafer 301 is sawed into individual dice for integrated circuits with individual circuit features. Nevertheless consistent performance may be expected from semiconductor devices employing such integrated circuits.

In CVD processes, a precursor is delivered to a CVD reactor in vapor form. In the case of solids and liquids, this requires heating of delivery line(s), CVD chamber and substrate. Siloxanes, particularly cyclosiloxanes, being susceptible to [Si—O] cleavage and polymerization, are more prone to such reactions in the presence of the heated delivery environment.

One of several chain initiating steps in the polymerization of siloxanes is the cleavage of the [Si—O] backbone or in the case of cyclosiloxanes the [Si—O] bond of the siloxane-ring. The present invention is useful in stabilizing materials containing siloxane compositions susceptible to such cleavage.

[Si—O] bond cleavage is homolytic or heterolytic, forming either free radical or ionically charged sites respectively. Whatever the mechanism, reactive sites are formed on the siloxane molecule, that may propagate to other molecules and polymerize. The chain reaction propagation continues until the reactive end of the chains is capped by "end-capping" radicals. The end-capping radical couples with the chain radical, and stops the chain propagation reaction.

Acids, bases, $H_2O$, and process gases such as $NH_3$, $CO_2$ and $O_2$ are common impurities in CVD processes involving dielectric thin films. When present, such impurities are capable of initiating the cleavage of [Si—O] backbone and/or ring-bonds, leading to premature polymerization reactions and irreproducible process conditions. Moreover, the reaction between such an impurities and a siloxane molecule is accelerated by the heated environment of the CVD process tool.

Advantageously, the present invention, in one embodiment, is directed to a stabilized cyclosiloxane dielectric precursor, comprising a siloxane reagent dosed with a stabilizing agent(s) selected from free-radical inhibitors, end-capping reagents and mixtures thereof. The free-radical inhibitor and/or end-capping reagent stabilize(s) the reactive sites on the siloxane molecule, through a quenching or capping mechanism, which advantageously reduces the occurrence of premature decomposition and deposition reactions.

Preferably, the bulk-siloxane reagent is purified prior to use as a precursor for dielectric thin film deposition. The purification process serves to reduce the concentration of impurities present in the bulk-siloxane reagent, thus extending its shelf-life and improving the process flows. The purification of the siloxane reagent however, addresses impurities attributable only to the siloxane reagent and fails to address impurities originating in the process delivery lines, and deposition chamber.

Siloxanes, particularly cyclosiloxane reagents may be purified by methods available and known to those skilled in the present art. Preferably, however, the siloxane reagent used in the present invention is purified by a process such as that disclosed in Applicant's co-pending U.S. patent application Ser. No. 10/015,326, filed on Dec. 31, 2001, entitled, "Method for Removal of Impurities in Cyclic Siloxanes Useful as Precursors for Low Dielectric Constant Thin Films" incorporated herein by reference in its entirety. Although the purification method disclosed therein reduces concentrations of water and trace acids in cyclosiloxanes to levels in the range of from about 1 to 20 ppm and from about 0.001 to 0.00001 wt %, respectively, small concentrations of residual impurities remain.

Moreover, the purification method thus disclosed in applicant's co-pending patent application fails to address impurities present in delivery lines and process hardware. Residual process gases, such as $NH_3$, from a previous etch-stop layer, deposition step, as described hereinabove and/or plasma source gases such as $O_2$ and $CO_2$, can back-stream into the source delivery lines, and cause premature deposition reactions through [Si—O] back-bone cleavage, ring-opening and/or polymerization reactions.

The present invention facilitates the use of siloxanes, particularly cyclosiloxanes as CVD precursors for low-dielectric constant thin films, by stabilizing the siloxane to prevent unwanted decomposition and polymerization, thus allowing cyclosiloxane based processes such as thin-film deposition, to be realized and controlled.

In one embodiment, the invention relates to a stabilized cyclosiloxane dielectric precursor including, a cyclosiloxane reagent dosed with a stabilizing agent selected from the group consisting of: free-radical inhibitors, end-capping reagents and mixtures thereof.

Siloxane reagents usefully stabilized by the present invention are preferably cyclosiloxanes having a structure according to the formula:

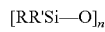

wherein each of R and R' is same or different and independently selected from the group consisting of hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl; and n is from 2 to 8. In a preferred embodiment, the cyclosiloxane is selected from the group consisting of: polyhedral oligomeric silsesquioxanes (POSS), octamethylcyclotetrasiloxane (OMCTS), more specifically 1,1,3,3,5,5,7,7-octamethylcyclotetrasiloxane (OMCTS), hexamethylcyclotetra-siloxane (HMCTS), more specifically 1,1,3,5,5,7-hexamethylcyclotetrasiloxane (HMCTS), tetramethylcyclotetrasiloxane (TMCTS), more specifically 1,3,5,7-tetramethylcyclotetrasiloxane (TMCTS), and mixtures thereof. In the most preferred embodiment, the cyclosiloxane to be stabilized is 1,3,5,7-tetramethylcyclotetrasiloxane (TMCTS).

As used herein the term end-capping reagent is defined as a reagent, which readily reacts with hydroxyl or radical groups resulting from cleavage of a [Si—O] bond of a siloxane backbone or cyclosiloxane ring, thereby forming a siloxane reagent having a non-reactive capped end. Useful end-capping agents include monofunctional-silylating agents having a formula R1R2R3SiX, wherein X is a reactive site, selected from but not limited to, H, OH, silyloxy and nitrogen-containing silyl, each of R1, R2 and R3 are same or different and independently selected from hydrogen, C1-C8 alkyl, C5-C12 aryl. Examples of useful end-capping reagents include but are not limited to napthylphenylmethylsilanol (NPMS), silyl-N-methylacetamides, trifluoropropyldimethylsilyl-N-methylacetamide (TFSA), bis(trimethylsiloxy)methylsilane, and hexamethyldisilanzane.

As used herein, a free-radical inhibitor is defined as a substance that stops free-radical polymerization of activated siloxanes by reacting therewith. In one embodiment, the free-radical inhibitor is a phenol and more preferably a hindered phenol, including but not limited to, butylated hydroxy toluene (BHT or called 2,6-di-tert-butyl-p-methylphenol), hydroquinone, diphenylamine and butylated hydroxy anisole (BHA or called 2,6-di-tert-butyl4-methoxyphenol).

In a further embodiment, the invention relates to a process for stabilizing a cyclosiloxane reagent including, purifying the cyclosiloxane reagent and dosing the cyclosiloxane reagent before, after or during purification with a stabilizing agent selected from the group consisting of: free-radical inhibitors, end-capping reagents and mixtures thereof.

The purification step to reduce the concentration of impurities in the siloxane reagent is optional and the actual dosing of the siloxane reagent with a stabilizing agent may occur at any point in the manufacturing process, including pre- or post-purification. Dosing the siloxane reagent before or during the purification step, (i.e. distillation) achieves higher siloxane reagent yields. However, dosing after the purification step is advantageous in that a predefined aliquot of stabilizing agent added to the siloxane reagent provides for accurate concentration calculations of stabilizing agent in the siloxane reagent.

In one embodiment, a cyclosiloxane reagent is dosed with a stabilizing agent in a total concentration range from about 0.01% to 10.0% by weight, more preferably in a total concentration range from about 0.05 to 1.00% by weight (including both end-capping and free radical inhibitor).

The purification step serves to reduce the concentration of impurities, including but not limited to water, acids and bases; and the dosing step serves to reduce [Si—O] bond cleavage in the cyclosiloxane ring. The purification step may include at least one of:

(1) contacting the cyclosiloxane reagent with an adsorbent bed material, so as to remove therefrom at least a portion of the water, and optionally at least one other impurity, to produce a cyclosiloxane precursor having a reduced level of water and optionally at least one other impurity; and removing the purified cyclosiloxane precursor from the adsorbent bed material; and (2) distilling a starting mixture comprising at least water and at least one cyclosiloxane CVD precursor, in the presence of an azeotropic component, so as to form an azeotropic mixture with the water contained in said starting mixture; in order to produce (A) a distillate fraction comprising water and the azeotropic component and (B) a balance fraction comprising cyclosiloxane, whereby said balance fraction (B) is substantially reduced in water relative to said starting mixture; and (3) a combination of 1 and 2;

and the dosing step includes addition of a free radical inhibitor, an end-capping agent or a combination thereof, to a cyclosiloxane reagent before, after or during the purification step.

In a further embodiment, the present invention relates to a CVD method of depositing a low dielectric constant thin film on a substrate from a stabilized cyclosiloxane reagent that has been dosed with a stabilizing agent selected from the group consisting of: free-radical inhibitors, end-capping reagents and mixtures thereof.

The CVD method may comprise the steps of:
placing the substrate in a chemical vapor deposition apparatus;
introducing at least one stabilized cyclosiloxane reagent into the apparatus;
vaporizing the stabilized cyclosiloxane reagent;
transporting the stabilized cyclosiloxane reagent vapor into a chemical vapor deposition zone containing the substrate, optionally using a carrier gas to effect such transport;
contacting the stabilized cyclosiloxane reagent vapor with the substrate under chemical vapor deposition conditions to deposit a thin film comprising an organosilicon composition; and
annealing the organosilicon thin film to produce a porous, SiCOH, low dielectric constant thin film.

The inert carrier gas in the processes described hereinabove may be of any suitable type, (e.g., argon, helium, etc.), or a compressible gas or liquid, (e.g., CO2).

The process described hereinabove preferably includes plasma enhanced CVD (PECVD). The plasma may be generated from single or mixed frequency RF power. The plasma source may comprise a high frequency, radio frequency (HFRF) plasma source component generating power in a range of from about 75 W to about 200 W at a frequency of about 13.56 MHz or a low frequency radio frequency (LFRF) plasma source component generating power in a range from about 5 W and 75 W at a frequency of about 350 kHz and/or combinations thereof. The plasma is maintained for a period of time sufficient to deposit the dense SiCOH thin film having retained therein a degree of the cage like structure of the original cyclosiloxane precursor.

In a preferred embodiment, the PECVD process is tuned with single frequency or dual frequency operating simultaneously to yield a dielectric thin film having retained therein between 1 and 50% and more preferably between 5% and 30% percent of the original cyclosiloxane cage like structure.

In a further embodiment, the dielectric thin film is post annealed in a furnace, at a temperature in the range of from about 100° C. to about 400° C., optionally in the presence of an oxidizing or reducing gas. Optionally the dielectric thin film may be annealed at a gradually increasing temperature profile. Preferably the dielectric thin film is annealed at a temperature of about 400° C.

Specific CVD conditions and more particularly PECVD conditions are readily determinable for a given application by empirically varying the process conditions (e.g., pressure, temperature, flow rate, relative proportions of the cyclosiloxane precursor gas and inert carrier gas in the composition, etc.) and developing correlation to the film properties produced in the process. The conditions of the process as disclosed herein are monitored to retain the cage like structure in the dense dielectric film.

The stabilized cyclosiloxane reagents may be employed in any suitable chemical vapor deposition system to form corresponding thin films on a substrate or microelectronic device precursor structure as a dielectric layer thereon. The CVD system may for example comprise a liquid delivery CVD system, a bubbler-based CVD system, or a CVD system of any other suitable type. Suitable liquid delivery CVD systems include those disclosed in Kirlin et al. U.S. Pat. No. 5,204,134; Kirlin et al. U.S. Pat. No. 5,536,323; and Kirlin et al. U.S. Pat. No. 5,711,816.

The PECVD method disclosed herein is an improvement over the prior art in that thin films are deposited from stabilized cyclosiloxane reagents having reduced levels of acidic impurities and water. By employing the stabilized cyclosiloxane reagents of the present invention the mean time to service of the CVD tool is reduced significantly and the reproducibility of the thin film process is improved.

The features, aspects and advantages of the present invention are further shown with reference to the following non-limiting example relating to the invention.

EXAMPLES

Example 1

A 12L flask equipped with a condenser, was charged with 5,000 grams of 1,3,5,7-tetramethylcyclotetrasiloxane (TMCTS) and 50 grams of CaH2 and a magnetic stir bar. The water content in the raw TMCTS was 125 ppm. The mixture was heated to reflux for about 10 hours with stirring under nitrogen protection. The condenser was then replaced by a distillation head and started to distill the TMCTS. After 170 g of fore-cuts was received, we collected 3470 grams of dry TMCTS. The water content in the dry TMCTS was analyzed to be below 5 ppm.

In a separate experiment, 100 grams of the raw TMCTS (with 125 ppm water) was mixed with 1 gram of CaH2 at room temperature. The mixture was magnetically stirred. The water content in TMCTS was monitored over time by taken out aliquots of TMCTS from the flask for water analysis. After 20 min, 2 hour and 4 hour drying at room temperature, its water content dropped to 12 ppm, 6 ppm and 2 ppm, respectively.

Example 2

In a dry box, a 100 mL flask equipped with a condenser, was charged with 50 grams of raw TMCTS and 2 grams of anhydrous CaO and a magnetic stir bar. The water content in the TMCTS was 125 ppm. The flask was taken out of the box. Under nitrogen protection, the TMCTS was refluxed for 10 hours. Then dry TMCTS was distilled over CaO. The water content in the distilled TMCTS was analyzed to be below 10 ppm.

Example 3

Raw TMCTS with 125 ppm water was mixed with 10% an azeotropic reagent in a distillation flask. The water content in the raw TMCTS was 125 ppm. After 20% TMCTS was distilled out azeotropically, the dried TMCTS was collected. The water contents in the dried TMCTS with different azeotropic agents are listed below:

TABLE 1

Water content in dried TMCTS after azeotropic distillation.

| Azeotropic agent | iso-Propyl alcohol | Di-iso-propyl ether | Toluene |
|---|---|---|---|
| Water content | <10 ppm | <20 ppm | 100 ppm |

Example 4

100 grams of raw TMCTS (with 125 ppm water) was mixed with 5 grams activated neutral molecular sieve at room temperature. After two days, an aliquot of TMCTS was taken and analyzed. Its water content was below 10 ppm.

Example 5

Raw TMCTS was mixed with 1% of MgSO4 at room temperature. TMCTS became very viscous overnight. NMR study revealed the TMCTS was completely polymerized.

Example 6

Figure 5A:
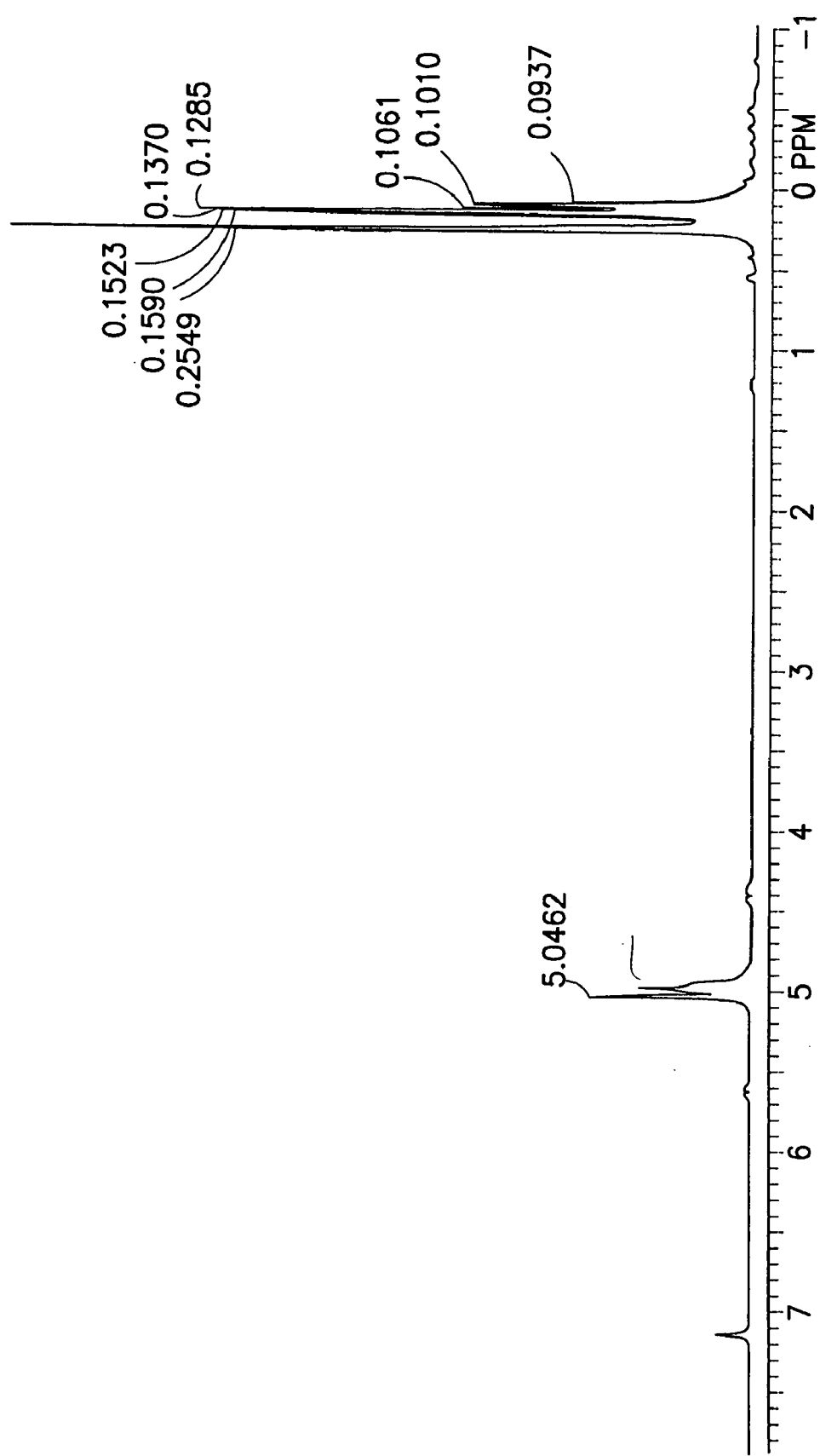
FIG. 5A is a 1H NMR spectrum of neat TMCTS in $C_6 D_6$ having 125 ppm water content after heating at 140° C. for 20 hours.
Figure 5B:
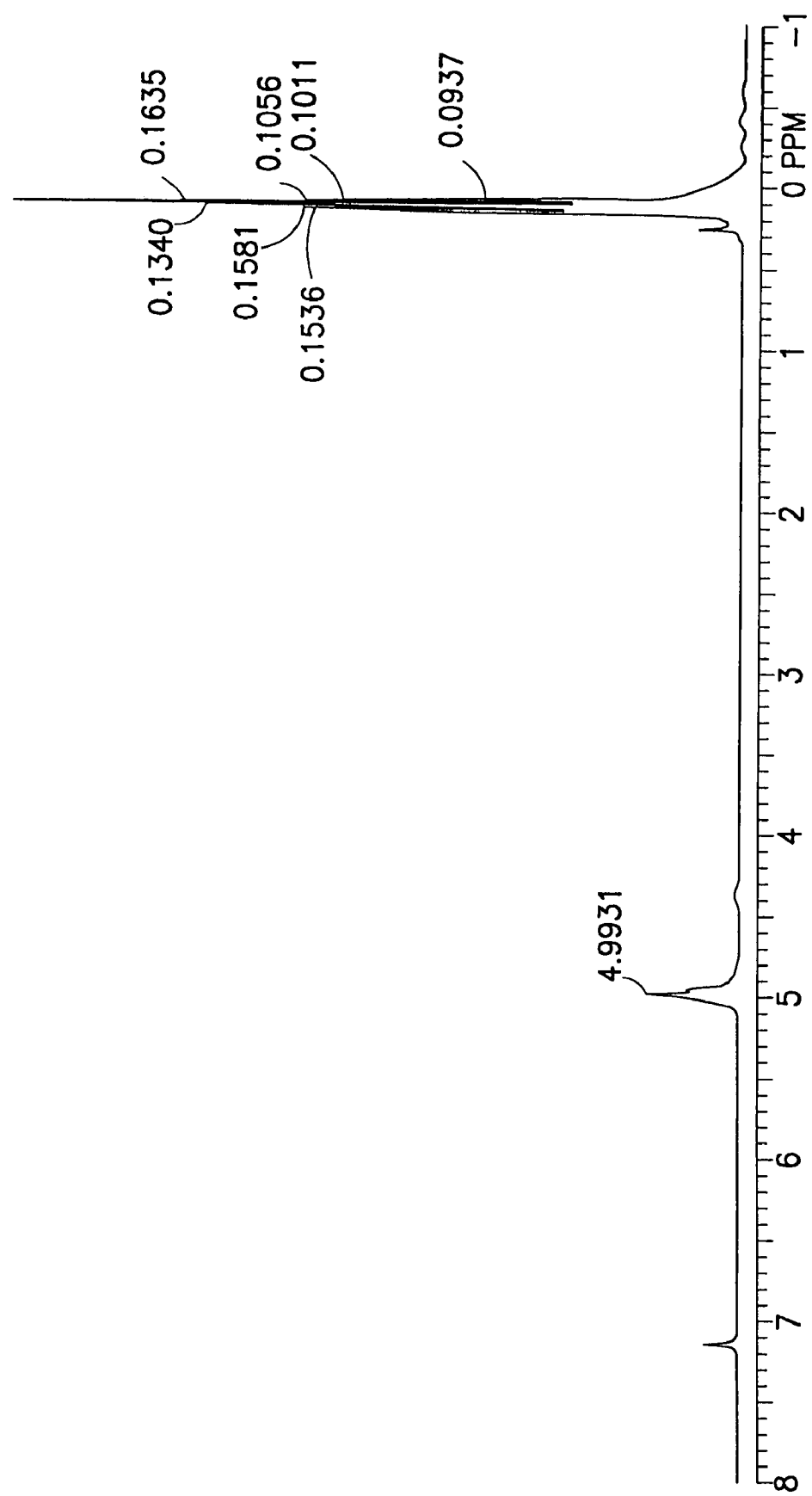
FIG. 5B is a 1H NMR spectrum of neat TMCTS in $C_6 D_6$ having <10 ppm water content after heating at 140° C. for 20 hours.

In an experiment to show the influence of water concentration on TMCTS polymerization, two samples of TMCTS having 125 ppm water and <10 ppm water respectively were heated at 140° C. for 20 hours and monitored by 1H NMR ($C_6 D_6$ solvent) for polymerization. FIG. 5A shows a 1H NMR spectrum for neat TMCTS having 125 ppm of water after 20 hours at 140° C. Although the cyclosiloxane Si—H and C—H resonance signals are present at 4.96 ppm and 0.14 ppm respectively, new resonance signals at 5.46 (Si—H) and (C—H) 0.26 ppm are indicative of polymer formation. Figure 5B shows a 1H NMR spectrum for neat TMCTS purified using a process including distillation and a drying agent as described hereinabove, and having <10 ppm water, after 20 hours at 140° C. Although to a lesser extent, polymerization reactions have occurred in the sample as indicated by a C—H resonance signal at about 0.26 ppm.

Example 7

A study of TMCTS thermal stability under oxygen ambient was conducted. TMCTS samples with additives (see Table 1) were heated at 80° C. in sealed quartz tubes. Additive A is, bis(trimethylsiloxy)methylsilane, additive B is BHT, dry TMCTS indicates less than 10 ppm of water and raw TMCTS indicates 69 ppm of water. Aliquots of the TMCTS were taken from each tube for analysis after 24 hour, 48 hour and 72 hour heating. The TMCTS assays are listed in Table 1.

TABLE 1

TMCTS thermal stability under $O_2$ and at 80° C.

| Heating time (hr) | Assay of dry TMCTS + 1% additive A (%) | Assay of dry TMCTS + 1% additive A (%) | Assay of raw TMCTS + 1% of additive A (%) | Assay of raw TMCTS + 1% of additive A (%) | Assay of dry TMCTS + 0.9% of additive A and 0.1% of additive B (%) | Assay of raw TMCTS + 0.9% of additive A and 0.1% of additive B (%) |
|---|---|---|---|---|---|---|
| 24 | 98 | 98 | 98 | 97 | 100 | 100 |
| 48 | 65 | 65 | 66 | 63 | 100 | 100 |
| 72 | 45 | 42 | 41 | 40 | 100 | 100 |

As shown from these results, there is no decomposition of TMCTS with 0.1% BHT while TMCTS without BHT shows significant polymerization under identical conditions (heating to 80° C. under an oxygen environment). The results conclusively support the importance of the free-radical polymerization mechanism and the ability of free-radical inhibitors, such as BHT, to greatly stabilize cyclosiloxanes having varying concentrations of water in an oxygen environment.

Example 8

Dried TMCTS thermal stability under ammonia (NH3) ambient was studied and results are summarized in Table 2. Ammonia used in this study contains approximately 2 ppm of water. TMCTS samples having additives as identified in Table 2 were heated at 80° C. in sealed quartz tubes and each experiment was repeated twice. Additive A is, bis(trimethylsiloxy)methylsilane, additive B is BHT, and dry TMCTS indicates less than 10 ppm of water. Aliquots of the TMCTS were taken from each tube for analysis after 24 hour, 48 hour and 72 hour heating. The TMCTS assays, as determined by $^1$H NMR are listed in Table 2.

As shown from the results in Table 2, there is negligible decomposition of TMCTS with 0.1% BHT and 0.9% bis (trimethylsiloxy)methylsilane, while TMCTS without bis(trimethylsiloxy)methylsilane shows slightly more polymerization under identical conditions (heating to 80° C. under an oxygen environment). The results conclusively support the importance of both free-radical inhibitors, such as BHT, and end-capping agents such as bis(trimethylsiloxy)methylsilane to greatly stabilize cyclosiloxanes in the presence of trace amounts of water and ammonia.

TABLE 2

Thermal Stability of Dried TMCTS Under $NH_3$ at 80° C.

| Time (hrs) | Assay of Dry TMCTS With 0.1% Additive B | Assay of Dry TMCTS with 0.1% Additive B | Assay of Dry TMCTS with 0.9% Additive A | Assay of Dry TMCTS with 0.9% Additive A | Assay of Dry TMCTS with 0.9% Additive A and 0.1% Additive B | Assay of Dry TMCTS with 0.9% A and 0.1% Additive B |
|---|---|---|---|---|---|---|
| 24 | 98% | 98% | 98% | 98% | 99% | 99% |
| 48 | 94% | 95% | 96% | 97% | 97% | 98% |
| 72 | 87% | 89% | 93% | 94% | 96% | 97% |

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth. To ensure uniform deposition of a dielectric film onto a substrate material, the dielectric precursor used in the film forming process must be stable at or until contacting the substrate material.

The invention claimed is:

1. A stabilized cyclosiloxane material for use as a dielectric precursor, the stabilized cyclosiloxane material comprising a cyclosiloxane reagent, an end-capping reagent, and a free radical inhibitor, wherein the end-capping reagent is selected from the group consisting of compounds of the formula $R^1R^2R^3SiX$ wherein:

each of $R^1$, $R^2$ and $R^3$ is independently selected from among H, $C_1$-$C_8$ alkyl and $C_5$-$C_{12}$ aryl; and X is selected from among $OH_1$ and nitrogen-containing silyl, and when any of $R^1$, $R^2$ or $R^3$ is $C_5$-$C_{12}$ aryl, then X can also be silyloxy.

2. The stabilized siloxane dielectric precursor according to claim 1, wherein said cyclosiloxane reagent is of the formula:

$$[RR'Si-O]_n$$

wherein each of R and R' is same or different and independently selected from the group consisting of hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl; and n is from 2 to 8.

3. The stabilized siloxane dielectric precursor according to claim 1, wherein said cyclosiloxane reagent is selected from the group consisting of: polyhedral oligomeric silsesquioxanes (POSS), octamethylcyclotetrasiloxane (OMCTS), hexamethylcyclotetra-siloxane (HMCTS), tetramethylcyclotetrasiloxane (TMCTS), and mixtures thereof.

4. A stabilized cyclosiloxane material for use as a dielectric precursor, the stabilized cyclosiloxane material comprising a cyclosiloxane reagent and an end-capping reagent wherein said cyclosiloxane reagent is 1,3,5,7-tetramethylcyclotetrasiloxane (TMCTS).

5. The stabilized siloxane dielectric precursor according to claim 1, wherein said end-capping reagent and said free radical inhibitor together form a stabilizing agent which is present in a concentration range from about 0.0 1% to 10.0% by weight based on a total weight of said material, and said end-capping reagent is selected from the group consisting of bis(trimethylsiloxy)methylsilane, silyl-N-methylacetamides, trifluoropropyldimethylsilyl-N-methylacetamide and hexamethyldisilanzane.

6. The stabilized siloxane dielectric precursor according to claim 1, wherein said stabilizing agent is present in a concentration range from 1.00 to 10.00% by weight.

7. The stabilized siloxane dielectric precursor according to claim 5, wherein said stabilizing agent comprises butylated hydroxyl toluene.

8. The stabilized siloxane dielectric precursor according to claim 1, wherein said end-capping agent reacts with hydroxyl or radical groups resulting from cleavage of a [Si—O] bond of the siloxane dielectric precursor.

9. The stabilized siloxane dielectric precursor according to claim 1, wherein X is nitrogen-containing silyl.

10. The stabilized siloxane dielectric precursor according to claim 1, wherein said end-capping reagent is selected from the group consisting of: napthylphenylmethylsilanol (NPMS), silyl-N-methylacetamides, trifluoropropyldimethylsilyl-N-methylacetamide (TFSA).

11. The stabilized siloxane dielectric precursor according to claim 5, wherein said stabilizing agent comprises a phenol.

12. The stabilized siloxane dielectric precursor according to claim 5, wherein said stabilizing agent comprises a hindered phenol.

13. The stabilized siloxane dielectric precursor according to claim 5, wherein said free radical inhibitor is selected from the group consisting of butylated hydroxy toluene (BHT), hydroquinone, butylated hydro anisole (BHA) and diphenylamine.

14. A process for stabilizing a cyclosiloxane dielectric precursor, including dosing a cyclosiloxane reagent with a stabilizing agent comprising an end-capping regent and a free radical inhibitor, to yield a stabilized cyclosiloxane material comprising the cyclosiloxane reagent, the end-capping reagent, and the free radical inhibitor, wherein the end-capping reagent is selected from the group consisting of compounds of the formula $R^1R^2R^3SiX$ wherein:
each of $R^1$, $R^2$ and $R^3$ is independently selected from among H, $C_1$-$C_8$ alkyl and $C_5$-$C_{12}$ aryl; and
X is selected from among OH, and nitrogen-containing silyl, and when any of $R^1$, $R^2$ or $R^3$ is $C_5$-$C_{12}$ aryl, the nX can also be silyoxy.

15. The process according to claim 14, wherein said stabilizing agent is present in a concentration range from about 0.01% to 10.0% by weight.

16. The process according to claim 14, wherein said stabilizing agent is present in a concentration range from about 0.05 to 1.00% by weight.

17. The process according to claim 14, further comprising a purification step.

18. The process according to claim 17, wherein said dosing occurs before, after or during said purification step.

19. The process according to claim 17, wherein said purification step is selected from the group consisting of
(1) contacting the cyclosiloxane dielectric precursor with an adsorbent bed material, so as to remove therefrom at least a portion of the water, and optionally at least one other impurity, to produce a cyclosiloxane precursor having a reduced level of water and optionally at least one other impurity; and removing the purified cyclosiloxane precursor from the adsorbent bed material; and
(2) distilling a starting mixture comprising at least water and at least one cyclosiloxane dielectric precursor, in the presence of an azeotropic component, so as to form an azeotropic mixture with the water contained in said starting mixture; in order to produce (A) a distillate fraction comprising water and the azeotropic component and (B) a balance fraction comprising cyclosiloxane, whereby said balance fraction (B) is substantially reduced in water relative to said starting mixture; and
(3) a combination of 1 and 2.

20. The process according to claim 17, wherein said purification step reduces concentrations of water and trace acids in cyclosiloxanes to levels in a range of from about 1 to 20 ppm and from about 0.001 to 0.00001 wt %, respectively.

21. A stabilized cyclosiloxane material for use as a dielectric precursor, the stabilized cyclosiloxane material comprising a cyclosiloxane reagent, and an end-capping reagent, wherein said cyclosiloxane reagent is selected from the group consisting of polyhedral oligomeric silsesquioxanes (POSS), hexamethylcyclotetra-siloxane (HMCTS), tetramethylcyclotetrasiloxane (TMCTS), and mixtures thereof, wherein the end-capping reagent is selected from the group consisting of compounds of the formula $R^1R^2R^3SiX$ wherein:
each of $R^1$, $R^2$ and $R^3$ is independently selected from among H, $C_1$-$C_8$ alkyl and $C_5$-$C_{12}$ aryl; and
X is selected from among OH, and nitrogen-containing silyl, and when any of $R^1$, $R^2$ or $R^3$ is $C_5$-$C_{12}$ aryl, then X can also be silyoxy.

22. The stabilized cyclosiloxane material of claim 21, dosed with a stabilizing agent comprising an end-capping reagent and optionally a free radical inhibitor.

23. The stabilized cyclosiloxane material of claim 22, wherein said stabilizing agent is present in a concentration from about 0.01% to about 10.0% by weight based on a total weight of said material.

24. The stabilized cyclosiloxane material of claim 23, where said end-capping reagent is selected from the group consisting of bis(trimethylsiloxy)methylsilane, silyl-N-methylacetamides, and trifluoropropyldimethylsilyl-N-methylacetamide.

25. The stabilized cyclosiloxane material of claim 24 comprising said free radical inhibitor, wherein said free radical inhibitor is selected from the group consisting of butylated hydroxy toluene (BHT), hydroquinone, butylated hydro anisole (BHA) and diphenylamine.

26. The stabilized cyclosiloxane material of claim 21, wherein said cyclosiloxane reagent is POSS.

27. The stabilized cyclosiloxane material of claim 21, wherein said cyclosiloxane reagent is HMCTS.

28. The stabilized cyclosiloxane material of claim 25, wherein said stabilizing agent comprises a phenol.

29. The stabilized cyclosiloxane material of claim 28, wherein said stabilizing agent comprises a hindered phenol.

30. The stabilized cyclosiloxane material of claim 24, wherein said end capping reagent is selected from the group consisting of silyl-N-methylacetamides, and trifluoropropyldimethylsilyl-N-methylacetamide.

31. The stabilized cyclosiloxane material of claim 24, wherein said end capping reagent is trifluoropropyldimethylsilyl-N-methylacetamide.

32. The stabilized cyclosiloxane material of claim 31, wherein said end capping reagent is selected from the group consisting of silyl-N-methylacetamides.

33. The stabilized cyclosiloxane material of claim 25 comprising said free radical inhibitor, wherein said free radical inhibitor is selected from the group consisting of butylated hydroxy toluene (BHT), hydroquinone, and butylated hydro anisole (BHA).

34. The stabilized cyclosiloxane material of claim 33 comprising said free radical inhibitor, wherein said free radical inhibitor is selected from the group consisting of butylated hydroxy toluene (BHT), and hydroquinone.

35. The stabilized cyclosiloxane material of claim 34 comprising said free radical inhibitor, wherein said free radical inhibitor is butylated hydroxy toluene (BHT).

36. A cyclosiloxane composition, comprising:
    (a) TMCTS;
    (b) stabilizer comprising BHT and bis(trimethylsiloxy)methylsilane, wherein the stabilizer is present in the composition in an amount of from about 1% to 10% by weight, based on the weight of TMCTS, and wherein the cyclosiloxane composition contains less than 10 ppm water.

* * * * *

UNITED STATES PATENT AND TRADEMARK OFFICE
CERTIFICATE OF CORRECTION

PATENT NO. : 7,423,166 B2  
APPLICATION NO. : 10/650282  
DATED : September 9, 2008  
INVENTOR(S) : Tianniu Chen Page 1 of 1

It is certified that error appears in the above-identified patent and that said Letters Patent is hereby corrected as shown below:

Column 8, line 14: "-butyl4" should be -- butyl-4 --.

Column 11, line 21: "F*igure*" should be -- Figure --.

Column 12, line 57: "$OH_1$" should be -- OH, --.

Column 13, line 15: "0.0 1%" should be -- 0.01% --.

Column 13, line 63: "the nX" should be -- then X --.

Column 14, line 46: "silyoxy" should be -- silyloxy --.

Signed and Sealed this

Sixteenth Day of December, 2008

JON W. DUDAS  
*Director of the United States Patent and Trademark Office*